(12) United States Patent
Goldsberry et al.

(10) Patent No.: US 8,568,751 B1
(45) Date of Patent: Oct. 29, 2013

(54) ANTI-AGING COSMECEUTICAL COMPOSITION

(75) Inventors: Susan Goldsberry, Huntington Beach, CA (US); Lyndon Garcines, Fountain Valley, CA (US)

(73) Assignee: Beachbody, LLC, Santa Monica, CA (US)

( * ) Notice: Subject to any disclaimer, the term of this patent is extended or adjusted under 35 U.S.C. 154(b) by 69 days.

(21) Appl. No.: 13/399,248

(22) Filed: Feb. 17, 2012

Related U.S. Application Data

(60) Provisional application No. 61/444,023, filed on Feb. 17, 2011.

(51) Int. Cl.
*A61K 8/02* (2006.01)

(52) U.S. Cl.
USPC .......................................................... 424/401

(58) Field of Classification Search
None
See application file for complete search history.

(56) References Cited

U.S. PATENT DOCUMENTS

2006/0210513 A1* 9/2006 Luizzi et al. ............... 424/70.13

* cited by examiner

*Primary Examiner* — Paul Dickinson
(74) *Attorney, Agent, or Firm* — Louis C. Paul

(57) ABSTRACT

Provided is a cosmeceutical composition that delivers both short and long term improvement in the appearance of skin. The composition includes, as required ingredients, at least a suspension of a powder of an aliphatic polyester copolymer, a cross-linked silicone elastomer, and one or more components that are hydrolyzates and/or acylated short chain peptides.

7 Claims, No Drawings

ANTI-AGING COSMECEUTICAL COMPOSITION

CROSS REFERENCE TO RELATED APPLICATION

This application claims priority to U.S. Provisional Application Ser. No. 61/444,023, filed on Feb. 17, 2011, the disclosure of which is incorporated herein by reference in its entirety.

FIELD OF INVENTION

The present invention is directed to compositions and methods for reducing the appearance of skin aging.
reference in its entirety.

SUMMARY OF THE INVENTION

The present invention is directed to an anti-aging cosmeceutical composition having a short-term skin appearance enhancing complex (STSE Complex) and a long-term skin enhancing complex (LTSE Complex). The STSE is comprised of: (i) an optical blurring tightening (OBT) complex, the OBT consisting essentially of (a) a suspension of a powder of a crosslinked polyester of adipic acid and neopentyl glycol, amodimethicone, dimethicone, hydroxypropyl methyl cellulose, vinyl pyrollidone/vinyl acetate copolymer, a modified vitamin C complex, citric acid, an acrylates/dimethicone copolymer and cyclopentasiloxane and (b) a crosslinked silicone elastomer and (ii) a facial muscle expression relaxing (FMER) agent, the FMER selected from the group of a protein hydrolyzate or a short-chain acylated peptide. The LTSE Complex is comprised of at least long-term anti-aging ingredient that reduces one or more of the number, amount or depth of facial fine lines and wrinkles, the anti-aging ingredient being selected from the group of protein hydrolyzates and short-chain acylated peptides.

DETAILED DESCRIPTION OF THE INVENTION

The topical anti-aging composition of the present invention provides short-term improvement, including near-immediate improvement in the appearance of facial skin, and long-term improvement in the appearance of facial skin, the improvement being selected from the group consisting of (a) reduction in one, preferably more than one, of the number, length and/or depth of superficial fine lines and wrinkles, (b) increased skin firmness and/or (c) reduction in skin laxity, the composition comprising.

In a preferred embodiment as further described below the topical anti-aging composition consists essentially of (i) a short-term skin enhancing complex (STSE Complex), and (ii) a long-term skin enhancing complex (LTSE Complex) that includes at least one protein hydrolyzate and/or acylated short chain peptide short chain peptide being clinically demonstrated to reduce, over time, the appearance of facial expression lines (e.g., crows feet, worry lines, frown lines).

Near-immediate improvement in the appearance of facial skin is achieved by filling facial fine lines and wrinkles.

Short-term improvement in the appearance of facial skin is achieved by reducing the contraction of facial expression lines. The short-term effect is one that typically lasts for less than 24 hours, sometimes for less than 12 hours.

Long-term improvement in the appearance of facial skin is achieved by visibly reducing the number, length and/or depth of superficial fine lines and wrinkles as measured with bioinstrumentation and/or clinical photography by methods known to the person having ordinary skill in the art of cosmetic formulation, including by methods described hereinbelow.

In one preferred embodiment, the composition of the present invention includes at least one, more preferably more than one, protein hydrolyzate, especially a hydrolyzate of a plant-derived protein, and/or acylated short chain peptide(s) that has been demonstrated to block neuromuscular contraction of facial expression muscles. Such compounds can be referred to as facial muscle expression relaxing agents (FMER-agents).

One preferred hydrolyzate and/or acylated short chain peptide(s) that is a FMER-agent that has been demonstrated to block neuromuscular contraction of facial expression muscle is Acetyl Hexapeptide-8 (formerly designated Acetyl Hexapeptide-3), and commercially available from Lipotec SA under the tradename Argireline®.

Another preferred hydrolyzate and/or acylated short chain peptide(s) that is a FMER-agent that has been demonstrated to block neuromuscular contraction of facial expression muscle is the hydrolyzate of protein isolated from *Hibiscus esculentus*, commercially available in combination with dextrin under the tradename Myoxinol® LS 9736 (INCI name Hydrolyzed *Hibiscus Esculentus* extract (and) Dextrin).

In more preferred embodiments, the composition of the present invention further includes, as constituents of the LTSE complex, at least one, preferably at least two of an acylated short chain peptide having eight or less amino acid residues, that visibly reduce the number, length and/or depth of superficial fine lines and wrinkles over time. For example, after 28 days of twice daily application of a particularly preferred embodiment of the present invention as shown in Example 1, the number, length and/or depth of superficial fine lines and wrinkles was visibly reduced.

Two particularly preferred acylated short chain peptide having eight or less amino acid residues are palmitoylated amino acid sequences Pal-GHK and Pal-GQPR, commercially available together from Sederma in an aqueous composition under the tradename Matrixyl® 3000 (INCI name Glycerine (and) Butylene Glycol (and) Carbomer (and) Polysorbate-20 (and) Palmitoyl Oligopeptide (and) Palmitoyl Tetrapeptide-3).

The short-term skin enhancing complex (STSE) includes an optical blurring and tightening complex (OBT Complex) having an optical blurring component as well as a tightening component. Together, the OBT Complex creates a perceptible short-term reduction in the appearance of facial fine lines and wrinkles.

The optical blurring component of the OBT Complex consists essentially of a suspension of (i) a powder of a synthetic crosslinked polymer, especially a crosslinked aliphatic polyester, preferably having a particle size in the range of 0.5-6μ, and (ii) a vinyl copolymer together with (iii) a Vitamin C Complex, as defined below, (iv) citric acid, and (v) Acrylates/Dimethicone (e.g. KP-545 from Shin-Etsu).

AuraSphere (available from Diow Industries, Inc.) is a preferred optical blurring suspension contains two primary polymers—Adipic Acid/Neopentyl Glycol Crosspolymer (40.0-50.0%) and VP/VA Copolymer (1.0-2.0%). Additionally, the AuraSphere Suspension contains Dimethicone (1.0-4.0%), Hydroxypropyl Methylcellulose (0.4-0.8%) and Amodimethicone (0.4-0.8%) and a non-paraben preservative system (Phenoxyethanol and Caprylyl Glycol and Chlorphenesin, commercially available under the tradename Microkill PCC) at concentration of from 0.75% to about 1.5%. The balance of the AuraSphere Suspension is water.

Adipic Acid/Neopentyl Glycol Crosspolymer is a copolymer of Adipic Acid and Neopentyl Glycol crosslinked by Isopropyltriethoxysilane.

VP/VA copolymer is a copolymer of vinyl acetate and vinylpyrrolidone monomers.

Dimethicone, also known as polydimethylsiloxane (PDMS) is polymeric organosilicon compound having the chemical formula

where n is the number of repeating units, $[SiO(CH_3)_2]$.

Amodimethicone is a siloxane polymer with amino functional groups and is represented by the formula:

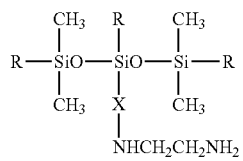

wherein R=OH, or $CH_3$; X=propyl, isopropyl or isobutyl

The optical blurring complex further comprises, as a required component, a "Vitamin C Complex" consisting essentially of ascorbic acid, corn starch, and silica.

In particularly preferred embodiments, the optical blurring component of the OBT Complex contains, as a required components, at least one, and preferably both of (i) citric acid, preferably in the form of fine powder and/or (ii) a graft copolymer of acrylic polymer and dimethylpolysiloxane in a volatile solvent, preference cyclopentasiloxane. A suitable graft polymer of this type is commercially available from Shin-Etsu Silicones under the tradename KP-545 (Acrylates/Dimethicone Copolymer (30%) in Cyclopentasiloxane (70%)).

The STSE Complex of the cosmeceutical composition of the present invention also includes, as a required component, a silicone elastomer.

Silicone elastomers useful in the STSE portion of the composition of the present invention are known in the art and may be obtained through various reactions. For example, they can be obtained by reacting a divinyl-terminated polysiloxane, preferably a poly (divinylpolydimethylsiloxane), with an organohydrogenpolysiloxane, preferably a copolymer of polydimethylsiloxane and polymethylhydrogensiloxane, the latter monomer optionally having at least one $C_{10}$-$C_{50}$ alkyl and/or phenyl side chain. KSG-16 (INCI name: Dimethicone and Dimethicone/Vinyl Dimethicone Crosspolymer), KSG-31 (INCI name: Squalane and Vinyl Dimethicone/Lauryl Dimethicone Crosspolymer, and USG-103 (INCI Name: Dimethicone/Vinyl Dimethicone Crosspolymer are examples of preferred silicone elastomers that are available from Shin-Etsu Chemical Co. Ltd.

Silicone elastomers may also be obtained by reacting an epoxy-containing compound, such as an epoxy-functional silicone, with an organohydrogenpolysiloxane by the process described in U.S. Pat. No. 5,128,431. Elastomers of this type are available from Momentive Performance Materials Inc. (Charleston, W. Va.) under the trade name Velvesil 125 (INCI name: Cyclopentasiloxane and $C_{30\text{-}45}$ Alkyl Cetearyl Dimethicone Crosspolymer).

The cosmeceutical composition of the present invention can and preferably does include at least one further volatile compound. By the term "volatile" is meant a fluid that has a measurable vapor pressure, preferably of at least about 2 mm of mercury at 20° C. Preferred volatile solvents generally have a viscosity of from about 0.5 to about 10 centipoise at 25° C. and are selected from the group consisting of volatile cyclic silicones, volatile linear silicones, volatile paraffinic hydrocarbons and mixtures thereof.

In particularly preferred embodiments, the composition of the present invention contain volatile water-immiscible materials selected from the group consisting of volatile silicones and volatile paraffinic hydrocarbons.

Additionally, in preferred embodiments, the composition of the present invention can and does include one or more of the following skincare anti-aging active ingredients: a glycosaminoglycan (GAG) or GAG precursor, preferably, Glucosamine HCl; an anti-inflammatory agent and/or an agent that reduces oxidative stress, a non-limiting, but preferred example of which is an extract of *Saccharomyces cerevisiae*; a moisturizing or humectant agent, a non-limiting, but preferred example of which is Urea; a vitamin or vitamin derivative, preferably ascorbic acid or citric acid; short chain peptides, preferably acylated and having up to 12 amino acids, that increase the expression of genes that code for collagen, elastin and/or defensins and/or that downregulate the expression of genes that code for matrix metalloproteinases or interleukins, non-limiting examples of which include Dipeptide-2; Dipeptide-4; Palmitoyl Dipeptide-7; Dipeptide Diaminobutyroyl Benzylamide Diacetate (SYN®-AKE); Tripeptide-1; Tripeptide-10 Citrulline (Decorinyl®); Palmitoyl Tripeptide-5 (SYN®-COLL); Copper Tri-Peptide; Acetyl Tetrapeptide-9 (DERMICAN™); Acetyl Tetrapeptide-11 (SYNIORAGE™; Palmitoyl Tetrapeptide-10; Acetyl Tetrapeptide-5 (Eyeseryl®); Palmitoyl Pentapeptide-4 (previously named Palmitoyl Pentapeptide-3, Matrixyl®); Pentapeptide-18 (Leuphasyl®); Pentapeptide-19; Acetyl Pentapeptide; Palmitoyl Hexapeptide-14 (previously named Palmitoyl Hexapeptide-6); Heptapeptide-6; Octapeptide-4; Acetyl Octapeptide-3 (also known as Acetyl Glutamyl Heptapeptide-3); Decapeptide-7; Oligopeptide-29 as well as the short-chain peptides disclosed in Paragraphs [0012]-[0081] of U.S. Patent Application Publication No. 2010/0144643, the disclosure of which is incorporated by reference; a sunscreen or sunblock.

Glucosamine HCL, *Saccharomyces cerevisiae* Extract and Urea are commercially available as part of the complex sold under the tradename UGL-II by Barnet Products Corp. (Englewood Cliffs, N.J.).

Reduction in the appearance of fine lines and wrinkles can be measured by a number of techniques known to those of skill in the art and including clinical assessment by a trained observer (e.g., doctor, nurse, or technician) or by biophysical instrument (e.g., by use of Silflo replica masks) or an imaging system such as VISIA from Canfield Scientific. Improvements in elasticity are measurable, for example, with a Twistometer. Reduction in the rate of transepidermal water loss and improvement in skin moisture content are measurable, respectively, with an evaporimeter and corneometer.

The anti-aging composition of the present invention, in one of its embodiments, is illustrated in the following non-limiting example.

EXAMPLE 1

Anti-Aging Cosmeceutical

| INCI Name | Wt/Wt % |
|---|---|
| Deionized Water | Q.S. |
| Xanthan Gum | 0.10-2.00 |

-continued

| INCI Name | Wt/Wt % |
|---|---|
| 1,3-Butylene Glycol | 1.00-5.00 |
| Hydrolyzed *Hibiscus Esculentus* Extract (and) Dextrin | 0.50-2.00 |
| Glycerin (and) Water (and) Butylene Glycol (and) Carbomer (and) Polysorbate 20 (and) Palmitoyl Oligopeptide (and) Palmitoyl Tetrapeptide-7 | 1.00-3.00 |
| Glucosamine HCL (and) Algae Extract (and) *Saccharomyces Cerevisiae* Extract (and) Urea | 1.00-5.00 |
| Sodium Citrate USP | 0.01-0.50 |
| Polysorbate 20 | 0.10-1.00 |
| Acetyl Hexapeptide-8 | 0.10-10.00 |
| Dimethicone | 1.00-5.00 |
| Cyclopentasiloxane | 2.00-10.00 |
| Dimethicone/Vinyl Dimethicone Crosspolymer, Cyclopentasiloxane | 2.00-10.00 |
| Lauryl PEG-9 Polydimethylsiloxyethyl Dimethicone | 0.50-3.00 |
| Adipic Acid/Neopentyl Glycol Crosspolymer, Water, Amodimethicone, Dimethicone Hydroxypropyl Methylcellulose, VP/VA Copolymer | 60.00-70.00 |
| Modified Vitamin C | 0.01-1.00 |
| Citric Acid, Powder USP | 0.01-1.00 |
| Acrylates/Dimethicone Copolymer (30%) (and) Cyclopentasiloxane (70%) | 0.01-3.00 |
| Phenoxyethanol (and) Hexylene Glycol (and) Ethyl Hexyl Glycerin | 0.50-2.00 |
| Zea Mays (Corn) Starch (and) Hydrolyzed Corn Starch (and) Hydrolyzed Corn Starch Octenylsuccinate (and) *Butyrospermum Parkii* (Shea) Butter (and) Phenylethyl Resorcinol (and) Lactic Acid (and) Cocamidopropyl Dimethylamine (and) Palmitoyl Tripeptide-5 | 0.01-3.00 |

It will be appreciated by those skilled in the art that changes may be made to the embodiments described above without departing from the spirit and scope of the present invention. It is understood, therefore, that this invention is not limited to the particular embodiments disclosed, but it is intended to cover modifications within the scope of the invention as defined by the appended claims.

The invention claimed is:

1. An anti-aging cosmeceutical composition having a short-term skin appearance enhancing complex (STSE Complex) and a long-term skin enhancing complex (LTSE Complex),
the STSE comprising
(a) an optical blurring tightening (OBT) complex, the OBT consisting essentially of
(i) a suspension of a powder of a crosslinked polyester of adipic acid and neopentyl glycol, amodimethicone, dimethicone, hydroxypropyl methyl cellulose, vinyl pyrollidone/vinyl acetate copolymer, a modified vitamin C complex, citric acid, an acrylates/dimethicone copolymer and cyclopentasiloxane; and
(ii) a crosslinked silicone elastomer;
(b) a facial muscle expression relaxing (FMER) agent, the FMER selected from the group of a protein hydrolyzate or a short-chain acylated peptide and
the LTSE Complex comprising at least long-term anti-aging ingredient that reduces one or more of the number, amount or depth of facial fine lines and wrinkles, the anti-aging ingredient being selected from the group of protein hydrolyzates and short-chain acylated peptides.

2. The anti-aging cosmeceutical composition of claim 1 wherein the LTSE Complex is comprised of at least two of a protein hydrolyzate or a short-chain acylated peptide.

3. The anti-aging cosmeceutical composition of claim 1 wherein the FMER-agent is selected from the group of acetyl hexapeptide-8, the hydrolyzate of a protein extracted from *Hibiscus esculentus*, or a combination of them.

4. The anti-aging cosmeceutical composition of claim 1 wherein the LSTE Complex contains Pal-GHK and Pal-GQPR.

5. The anti-aging cosmeceutical composition of claim 1 further comprising an antioxidant vitamin.

6. The anti-aging cosmeceutical composition of claim 5 wherein the antioxidant vitamin is selected from the group consisting of citric acid, ascorbic acid, or a combination thereof.

7. The anti-aging cosmeceutical composition of claim 1 wherein the composition is in the form of a silicone in water emulsion.

* * * * *